United States Patent [19]

Nurmamedov et al.

[11] Patent Number: 4,871,362

[45] Date of Patent: Oct. 3, 1989

[54] INTRAOCULAR LENS

[75] Inventors: Narzy N. Nurmamedov; Valery I. Gonchar; Babamurad A. Bazarov; Arslan Nurmukhamedov; Irina V. Skrylnikova, all of Ashkhabad; Ilyas A. Mustaev; Valery L. Varshavsky, both of Moscow, all of U.S.S.R.

[73] Assignee: Otdelenie Vsesojuznogo Nauchno-Issledovatelskogo I Proektno-Konstruktorskogo Tekhnologicheskogo, Ashkhabad, U.S.S.R.

[21] Appl. No.: 222,359

[22] Filed: Jul. 20, 1988

Related U.S. Application Data

[63] Continuation of Ser. No. 22,661, Mar. 6, 1987, abandoned.

[51] Int. Cl.$^4$ .............................................. A61F 2/16

[52] U.S. Cl. ........................................................ 623/6
[58] Field of Search ............................................ 623/6

[56] References Cited

U.S. PATENT DOCUMENTS

| 4,159,546 | 7/1979 | Shearing | 623/6 |
| 4,251,887 | 2/1981 | Anis | 623/6 |
| 4,316,292 | 2/1982 | Alexeev | 623/6 |
| 4,666,445 | 5/1987 | Tillay | 623/6 |

FOREIGN PATENT DOCUMENTS 563174 6/1977 U.S.S.R. ................................. 623/6

Primary Examiner—Ronald L. Frinks
Attorney, Agent, or Firm—Burgess, Ryan & Wayne

[57] ABSTRACT

An intraocular lens, comprising an optic lens and supporting elements made of a material possessing the effect of plastic memory in hot and cold states.

6 Claims, 2 Drawing Sheets

INTRAOCULAR LENS

This application is a continuation of application Ser. No. 022,661, filed Mar. 6, 1987, now abandoned.

FIELD OF THE INVENTION

The invention relates to medicine and more specifically to ophthalmology and concerns intraocular lenses.

BACKGROUND OF THE INVENTION

At present one of the most critical problems in ophthalmological practice is how to correct vision after cataract extraction.

There exist a number of methods for such correction, e.g., spectacles or contact lenses. However, sight correction with the aid of spactacles fails to restore patient's normal visual acuity, while correction with the help of contact lenses is not tolerated well by all patients, especially by aged persons (about 80 to 85 percent) when cataract is most commonly encountered.

That is why ophthalmologists throughout the world have sought for other ways to solve this problem. Another solution of the aforesaid problem is intraocular correction, i.e., implantation of a prosthetic lens.

There are known a variety of constructions of intraocular lenses, a majority of which are for implantation in the anterior eye chamber and for securing to the iris or in the crystalline capsule, where the lens supporting elements are fixed by a suture. Such intraocular lenses are obviously far from meeting all requirements indispensable for full sight correction.

The most successful is an intraocular lens adapted for intracapsular implantation. An eye with an intracapsularly implanted intraocular lens differ in nothing from a normal phakial eye. The crystalline capsule isolates the intraocular lens from the surrounding tissues, thus absolutely precluding its dislocation, while close mutual arrangement of the intraocular lens centre and the centre of a natural crystalline lens helps attain binocular vision in the case of uni- or bilateral aphakia.

However, for successful and more complete sight correct by virtue of intracapsular implantation, use should be made of intraocular lenses based upon a novel principal of intraocular lens fixation in human's eye.

Known in the art is an intraocular lens (cf. USSR Inventor's Certificate No. 563,174, Int.Cl. A 61 F 9/00) having a securing and a supporting element. Both of the elements are substantially identical and are shaped as loop-shaped legs made of a rigid material and fastened on the lens lateral surface, the only difference being in that the securing element has two projections for the suture material to guide and hold. Such a lens is adapted for being implanted in the crystalline capsule.

However, implantation of such an intraocular lens involves a long operative wound commensurable with the overall dimensions of the lens, the supporting elements inclusive. Moreover, the necessity of stitching the eyelets of the securing elements to the lips of the incision in the iris sophisticates the implantation technique of said intraocular lens.

There is also known an intraocular lens (cf., e.g., U.S. Pat. No. 4,316,292, Int.Cl. A 61 F 1/16, issued on Feb. 23, 1982), comprising an optical lens provided with supporting and fastening elements which are fixed to the lens on the diametrically opposite sides thereof, the fastening element being essentially a radially displaceable loop-shaped lug from an elastic material.

The implanting of an intraocular lens in the crystalline capsule of a patient is carried out as follows. After an extracapsular cataract extraction a special calibrated spatula is inserted into the empty crystalline capsule and the distance from the equator to the centre of the crystalline capsule is measured.

Then the supporting element of the intraocular lens made as a loop-shaped lug is either bent out or bent in so as to obtain a distance to the lens centre, corresponding to the distance from the crystalline capsule to the centre of the pupil.

After matching the required parameter of the intraocular lens, the latter is introduced into the crystalline capsule, and the fastening element is stitched up to the basal iridotomy.

However, the aforediscussed implantation of the intraocular lens mentioned above requires a large operative incision, additional devices in the form of a calibrated spatula, and a very high lens adjusting accuracy with the respect to the eye optic axis and, first and foremost, such implantation involves fixing the fastening element in the eye by stitching, which is a very complicated task from technical viewpoint.

Another intraocular lens is also known to comprise an optic lens and radially arranged supporting elements made as rods with rounded-off ends (cf., e.g., U.S. Pat. No. 4,159,546, Int.Cl. A 61 F 1/16; A 61 F 1/24 issued on July 3, 1979).

The aforediscussed intraocular lens is implanted in the posterior eye chamber through the dilated pupil and an incision made in the anterior portion of the crystalline capsule by compressing the supporting element during the implantation procedure and by resting against the ciliary body, followed by fitting the entire lens in a ture position within the posterior chamber.

Such a construction of the intraocular lens requires very high skill on the part of the ophthalmosurgeon for its implantation, since the surgeon must select the efforts to be applied during the implantation at a high degree of accuracy so as to introduce the lens proper into the posterior chamber and to compress the supporting element. Even minutest inaccuracy comitted during the implantation procedure might inflict damage to the patient's eye components.

Another disadvantage of the construction of said intraocular lens consists in that its resting upon the posterior chamber equator occurs substantially at one point on each of the supporting elements, which brings about inevitable vibration of the lens and hence an indistinct image, on the ocular retina, of a visually percepted object while in motion.

ESSENCE OF THE INVENTION

It is an object of the invention to provide such an intraocular lens that would enable, due to appropriately implemented supporting elements, to considerably reduce the degree of traumaticity of the implantation procedure and simplify said procedure.

This and other objects of the invention are accomplished due to the fact that in an intraocular lens comprising an optic lens, a plurality of supporting elements rigidly fixed to the optic lens and radially arranged thereon, said elements being shaped as rods and having their ends bent out, according to the invention, the supporting elements are made of a material possessing a plastic memory quality (transformation-induced plasticity) both in hot and cold state.

This feature reduces much the degree of traumatism of the implantation procedure and simplifies the latter.

It is expedient that the supporting elements of the intraocular lens shaped as rods be arranged in a plane square with the principal optic axis of the lens and a portion of the bent-out end of each rod be situated on a circle corresponding to the equator of the crystalline capsule.

This provides for reliable fixation of the intraocular lens in the crystalline capsule.

It is practicable that the bent-out end of the supporting element of the intraocular lens be held rigidly to the lens lateral surface.

This rules out vibration of the intraocular lens in the crystalline capsule.

SUMMARY OF THE DRAWINGS

In what follows the invention will be explained in some specific embodiments thereof to be read in conjunction with the accompanying drawings, wherein.

DETAILED DESCRIPTION OF THE INVENTION

Figure 2:
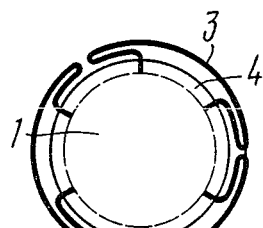
FIG. 2 is a schematic front elevational view of an intraocular lens showing the free bent-out end of the rod rigidly fixed on the lens and prepared for implantation, according to the invention.
Figure 3:
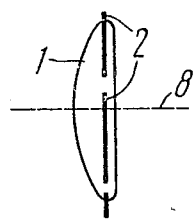
FIG. 3 is a schematic side elevational view of an intraocular lens prepared for implantation, according to the invention.
Figure 6:
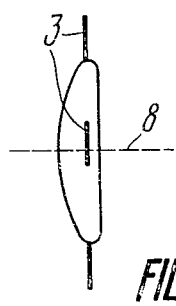
FIG. 6 is a schematic side elevational view (post-implantation) of the intraocular lens of FIG. 4, according to the invention.
Figure 10:
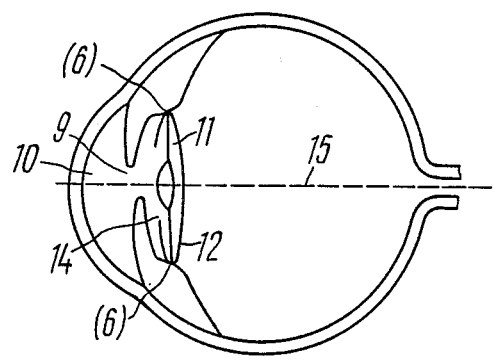
FIG. 10 is a schematic cross-sectional view of a human eye to illustrate the position of the implanted intraocular lens therein, according to the invention.

The intraocular lens as disclosed in the present invention, comprises an optic lens 1 (FIGS. 1, 2) of any of the heretofore-known constructions, e.g., planoconvex as shown in FIGS. 3, 6 and supporting elements 2 and 3 spaced equidistantly along the periphery of the lens 1 and held to a lateral peripheral surface 4 of the lens 1 by any hitherto-known technique. The supporting elements 2, 3 are made of an alloy possessing thermomechanically induced plasticity (plastic memory) in hot and cold states within a temperature interval of shape restoration in a hot and a cold state of between about 35° C. and 20° C.

Figure 1:
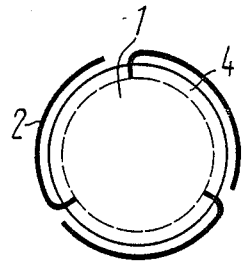
FIG. 1 is a schematic front elevational view of an intraocular lens prepared for implantation, according to the invention.

FIGS. 1, 2, 3 represent intraocular lenses having the supporting elements 2, 3 placed on the peripheral lateral surface of the lens 1 and prepared for implantation at 20° C. (while in a cooled state).

Figure 4:
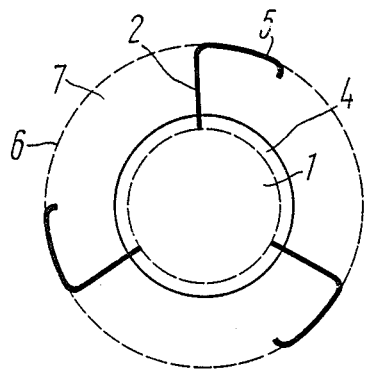
FIG. 4 is a schematic front elevational view (post-implantation) of the intraocular lens of FIG. 1, according to the invention.
Figure 5:
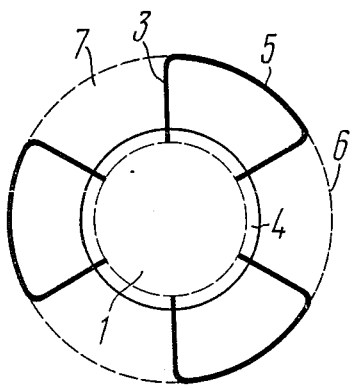
FIG. 5 is a schematic front elevational view (post-implantation) of the intraocular lens of FIG. 2, according to the invention.

FIGS. 4, 5, 6 illustrate intraocular lenses with th supporting elements 2, 3 in a developed state after their having been implanted in the patient's eye at body temperature (35° to 36°). The supporting elements are so made that a portion of a bent-out end 5 (FIGS. 4, 5) of each rod (2, 3) lies within a circle 6 which corresponds to the equator of the crystalline capsule.

The bent-out ends of the rods of the supporting elements 2, 3 lie in a plane 7 square with a principal optic axis 8 of the lens (FIGS. 3, 4, 5, 6). The bent-out end of each of the rods of the supporting elements 2 may be free (FIGS. 1, 4). The free (unsecured) ends of the supporting elements 3 made as rods with bent-out ends may be rigidly fixed on the lateral surface of the lens 1 (FIGS. 2, 5).

The implanting procedure of the intraocular lens, according to the invention, is carried out as follows (FIGS. 7, 8, 9, 10).

Once an extracapsular cataract extraction has been performed an anterior eye chamber 10 and an interior space 11 of a crystalline capsule 12 are filled with physiological saline cooled down to about 15° or 20° C.

Figures 7, 8, 9:
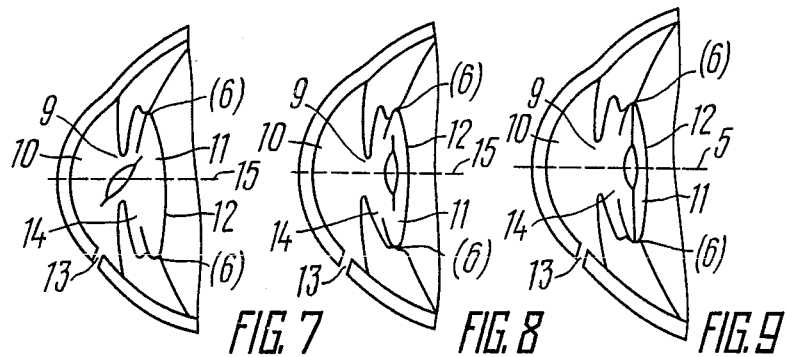
FIGS. 7 through 9 illustrate individual consecutive stages of the implantation procedure of an intraocular lens, according to the invention.

Preparatory to implantation the intraocular lens is cooled in physiological saline having a temperature below plus 20° C. (which corresponds to the point of forward martensite transformation) at which the supporting elements 2 or 3 assume a compressed shape preset in a cold state (FIGS. 1, 2). Then, by gaining access through the operational incision made in a cornea 13 and via an opening 14 in the front portion of the crystalline capsule and by making use of any suitable holder, such as needle, forceps, etc. (omitted in the drawing), one should insert a cooled intraocular lens with the supporting elements 2 or 3 (FIGS. 1, 2) in the collapsed state, into the interior space 11 (FIG. 7) of the crystalline capsule 12 and to orient the lens in such way that the optic axis 8 of the lens 1 be arranged square with the equatorial plane 7 of the crystalline capsule 12 (FIG. 8).

Next physiological saline warmed up to plus 35° C. is administered into the anterior chamber 10 and the interior space 11 of the crystalline capsule 12. While so doing the intraocular lens is kept inside the crystalline capsule 12 (FIG. 8) as it has been stated above. As the material of which the supporting elements 2 or 3 are made acquires the temperature at which shape restitution in a hot state occurs (the point of reverse martensite transformation) which equals to human body temperature, the supporting elements 2 or 3 (FIGS. 4, 5) restore its previous shape and, while extending, rest upon the equator 6 of the crystalline capsule 12, thus fixing and centering the optical axis 8 of the lens 1 within the zone of an eyeball optic axis 15 (FIG. 9). Such an arrangement of the supporting elements 2 or 3 (FIGS. 9, 10) of the intraocular lens in the crystalline capsule 12 makes it possible to reliably fix the lens inside the capsule 12 along the inner circumference 6 of its equator due to its resting upon the bent-out portions 5 of the supporting elements 2 or 3 arranged on the circumference 6 of the equator of the crystalline capsule 12.

The intraocular lens retains its proper position in the eye (as illustrated in FIGS. 4, 5, 6) by virtue of the patient's body temperature.

Whenever it is necessary to remove the intraocular lens, the anterior eye chamber 10 and the interior space 11 of the crystalline capsule 12 are to be cooled down to a temperature below plus 20° C. As a result, the supporting elements 2 or 3 assume the shape preset in a cold state and collapse along the peripheral lateral surface 4 of the lens 1 (FIGS. 1, 2, 3), whereupon the intraocular lens can easily be removed.

Application of an alloy possessing thermomechanically induced plasticity in hot and cold states establishes substantial distinction between the intraocular lens of the invention and such lenses known heretofore, since the ability of the material of the supporting elements 2, 3 to restore a preset shape upon being heated to the temperature of a patient's body renders the operational procedure less complicated and time-consuming and dispenses with attachment of the lens with sutures.

In addition, equidistant spacing of the three supporting elements 2, 3 along the equator 6 of the capsule 12 of the extracted natural crystalline lens provides for reliable fixing of the lens 1, the lens vibration is diminished, since the material of which the supporting elements are made, features 'superelasticity' within the temperature range of the reverse martensite transformation (i.e., shape restitution in a hot state). Apart from this, application of the intraocular lens disclosed in this invention involves retention of the functions of the pupil and iris of a human eye and prevents intra-and postoperative complications, i.e., traumatic lesions of the corneal and iridal endothelium, rules out lens dislocation into the anterior chamber or vitreous humor.

The intraocular lens of the invention has a low weight, since the alloy from which the supporting elements are made, features a low density.

The construction of the intraocular lens is simple and reliable in implantation, which is accounted for by the nature of a phase (crystalline) structural transformation which underlies the effect of thermomechanical plastic memory. The alloy used for the supporting elements 2, 3 is chemically and biologically inert, features high strength and is nonmagnetic. In addition, the intraocular lens being disclosed is easily removable from the eye.

We claim:

1. An intraocular lens, for implantation in the eye comprising an optic lens having a principal optic axis and provided with supporting elements radially arranged and rigidly fixed on said lens; said supporting elements shaped as rods with bent-out ends and made of a material that automatically deforms said supporting elements into a contracted configuration when subjected to a temperature at least as cold as a first predetermined temperature and that automatically deforms said supporting elements into an expanded configuration when subjected to a temperature at least as hot as a second predetermined temperature higher than said first predetermined temperature said supporting elements when expanded exhibiting bends in said elements to provide a different configuration than when said elements are in said contracted state.

2. An intraocular lens as claimed in claim 1, wherein said rods are located in a plane square with the principal optic axis of said lens and at least part of said bent-out end of each said rod lies on a circle corresponding to the equator of the crystalline capsule.

3. An intraocular lens as claimed in claim 2, wherein said bent-out end of each of said rods is attached to a lateral surface of said lens.

4. An intraocular lens as claimed in claim 1, wherein said first predetermined temperature is about 20° C. and said second predetermined temperature is about 36° C.

5. An intraocular lens as claimed in claim 1, comprising an optic lens having a principal optic axis and provided with supporting elements radially arranged and rigidly fixed on said lens; said supporting elements shaped as rods with both ends attached to said lens and having a bent-out portion, said rods made of a material that automatically deforms said supporting elements into a contracted configuration when subjected to a temperature at least as cold as 20° C., and that automatically deforms said supporting elements into an expanded configuration when subjected to a temperature at least as hot as 36° C.

6. An intraocular lens as claimed in claim 1 wherein said bent-out portion lies within a circle corresponding to the equator the crystalline capsule of said eye, and the remaining portion of said element is affixed to said lens and is essentially in alignment with a line drawn to the center of said lens.

* * * * *